United States Patent [19]

Colombo et al.

[11] Patent Number: 5,786,290

[45] Date of Patent: Jul. 28, 1998

[54] CATALYST AND PROCESS FOR PREPARING LONG CHAIN ALKYLAROMATIC COMPOUNDS

[75] Inventors: Giovanni Colombo, Inveruno; Stefano Amarilli, Maggiora, both of Italy; Imre Kiricsi, Szeged, Hungary; Carlo Perego, Carnate, Italy

[73] Assignee: Enichem Agusta S.p.A., Palermo, Italy

[21] Appl. No.: 545,875

[22] Filed: Oct. 20, 1995

[30] Foreign Application Priority Data

Nov. 10, 1994 [IT] Italy ................................. MI94A2274

[51] Int. Cl.⁶ ........................ B01J 21/16; B01J 29/04; C07C 2/66

[52] U.S. Cl. .......................... 502/84; 502/61; 502/63; 502/73; 502/74; 585/468

[58] Field of Search ........................ 502/61, 63, 73, 502/74, 84, 251, 252, 253, 259, 260, 263; 585/467, 468

[56] References Cited

U.S. PATENT DOCUMENTS

| | | | |
|---|---|---|---|
| 4,666,877 | 5/1987 | Vaughan | 502/84 |
| 5,059,568 | 10/1991 | McCauley | 502/65 |
| 5,068,216 | 11/1991 | Johnson et al. | 502/241 |
| 5,308,812 | 5/1994 | Salem et al. | 502/63 |

FOREIGN PATENT DOCUMENTS

| | | |
|---|---|---|
| 0 400 857 | 12/1990 | European Pat. Off. . |
| 0 437 132 | 7/1991 | European Pat. Off. . |
| 2 563 446 | 10/1985 | France . |
| WO 89/00083 | 1/1989 | WIPO . |

*Primary Examiner*—Glenn Caldarola
*Assistant Examiner*—Thuan D. Dang
*Attorney, Agent, or Firm*—Oblon, Spivak, McClelland, Maier & Neustadt, P.C.

[57] ABSTRACT

A catalyst is disclosed which comprises a clay belonging to the family of smectites, containing multi-metal pillars, together with a process which uses such a catalyst for the alkylation of aromatic hydrocarbons by means of long chain linear olefins. The resulting alkyl-aromatic compounds are useful for preparing biodegradable synthetic detergents.

8 Claims, No Drawings

CATALYST AND PROCESS FOR PREPARING LONG CHAIN ALKYLAROMATIC COMPOUNDS

BACKGROUND OF THE INVENTION

1. Field of the Invention

The present invention relates to a catalyst comprising a clay belonging to the family of smectites, containing multimetal pillars; as well as to a process using such a catalyst for the alkylation of aromatic hydrocarbons by means of long chain linear olefins.

2. Description of the Background

The alkyl aromatic compounds are useful in a plurality of commercial applications. Among these, the most important application is their use in the preparation of biodegradable synthetic detergents. Processes for preparing aromatic compounds using catalysts of Friedel-Crafts type, such as, e.g., $AlCl_3$, $BF_3$, $H_2SO_4$ and HF, has been long known. Unfortunately, these catalysts display, obviously, considerable drawbacks, because they cause corrosion problems in the used materials, as well as environmental problems associated with the disposal of the processing wastes.

Subsequently, some solid catalysts were found which are useful for performing the alkylation of aromatic hydrocarbons with olefins, yielding a production of comparable quality to the preceding one, however without the above said environmental and corrosion problems. Therefore, suitably treated zeolites and clays were used for that purpose. The latter can be both from natural sources and synthetic, exchanged with metal cations. For example, in U.S. Pat. No. 4,460,826, a natural or synthetic tri-octahedral clay exchanged with metal cations is used for alkylating benzene with long chain olefins. U.S. Pat. No. 4,499,319 claims the use of layered clays with laminar structure, such as montmorillonite, exchanged with such metal cations as chromium and aluminum, for the alkylation of aromatic compounds with alkylating agents containing less than 6 carbon atoms. Cation-exchanged and then suitably activated synthetic clays useful for alkylating aromatic compounds, are disclosed in U.S. Pat. No. 4,075,126. In EP-353,813, for the catalytic alkylation of aromatic hydrocarbons with olefins, either natural or synthetic zeolites, amorphous silico-aluminas, clays or their mixtures, possibly submitted to ionic exchange with aluminum, chromium or rare earths salts, are used.

However, metal cation exchanged clays showed poor heat stability. Therefore, as alkylation catalysts, modified clays were subsequently used which are referred to as "pillared clays", which, in comparison to the above disclosed materials, are relatively stable also at high temperatures.

These materials are prepared by starting from either synthetic or natural clays, such as, e.g., smectites, vermiculites or bentonites. The clays are constituted by layers of semi-crystalline alumino-silicate bonded to each other by electrostatic van der Waals forces. The anionic charges on silica layers are neutralized by cations situated inside the interlaminar spaces. These cations, usually $Na^+$ and $Ca^{2+}$, can be exchanged with monomeric, oligomeric or polymeric species derived from metal hydroxides, such as, e.g., hydroxo-polymeric cations

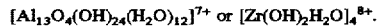
$[Al_{13}O_4(OH)_{24}(H_2O)_{12}]^{7+}$ or $[Zr(OH)_2H_2O]_4^{8+}$.

Such cations act as a separation system for crystalline silico-aluminate planes, i.e., as a pillaring system. EP-83,970 discloses the use of a clay in which alumina pillars are anchored inside the interior of the laminar structure, for benzene alkylation with light olefins. In U.S. Pat. No. 5,034,564, a pillared clay containing an oxide of a metal selected from Al, Zr, La, Ce and Ti as spacer element for crystalline planes, co-extruded with a binder, is used in aromatic hydrocarbons alkylation reactions.

In Applied Catal., 14, 69–82 (1985) by M. L. Occelli, an Na montmorillonite layered with a system of aluminum oxide clusters, is compared to other catalyst types in toluene ethylation reactions.

These catalysts should display a high heat stability, also in the presence of water, in order to be able to withstand the regeneration treatments which are carried out in the presence of an oxidizer agent, such as air or oxygen, and which cause water to be simultaneously formed.

Catalysts with improved heat stability both when dry and in the presence of moisture are disclosed in U.S. Pat. No. 4,248,739, relating to the use of high molecular weight complex cations for clay pillaring, and in U.S. Pat. No. 4,963,518, in which the stabilization treatment of pillared clays by means of a silylating agent is disclosed. A method to increase the distance between clay layers, with the stability of clay being retained, consists in pretreating clays with non-ionic organic compounds, such as polyvinyl alcohol, and then submitting them to pillaring treatment (K. Suzuki et al. Clays and Clay Miner., 1988, 36, 147–152).

Also pillared clays are known which contain simultaneously two intercalating metals, i.e.: gallium and aluminum (A. V. Coelho, G. Ponclet, Appl. Catal., 1991, 77, 303–314), aluminum and iron (F. Bergaya et al., Stud. Surf. Sci. Catal., Preparation of catalysts V., 1991, 329–336), lanthanum and nickel (A. K. Ladavos et al., Stud. Surf. Sci. Catal., Preparation of catalysts V., 1991, 319–328), aluminum and rare earths (J . Serte, Stud. Surf. Sci. Catal., Preparation of catalysts V., 1991, 301–310).

In U.S. Pat. No. 4,666,877, a pillared clay is disclosed which is prepared by treating a smectite with a pillaring agent consisting of a hydroxo-polymer cation with formula

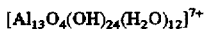
$[Al_{13}O_4(OH)_{24}(H_2O)_{12}]^{7+}$ in which some aluminum ions have been replaced by transition metals, to yield a polyoxo metallic ion having formula

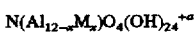
$N(Al_{12-x}M_x)O_4(OH)_{24}^{+a}$ in which N is selected from Al, Si, Ga, Ge, As, P, Cr, Fe, V, Ru, or Ni, and M is selected from V, Cr, Mn, Fe, Co, Ni, Nb, Mo, Te, Ru, Rh, Pd, Ta, W, Re, Os, Ir, Pt. These materials are useful as catalysts for conventional processes of petroleum transformation, such as cracking, hydrocracking, isomerization, reforming and polymerization.

It has now been found that a pillared clay containing pillars of alumina and particular metals is useful as a catalyst for preparing linear alkyl aromatic products. Such a catalyst is more active, selective and more thermally stable than the catalysts known in the prior art.

SUMMARY OF THE INVENTION

Accordingly, one object of the present invention is to provide a catalytic material comprising a smectite containing pillars of aluminum oxide, pillars of oxide of an "A" metal selected from cerium, cobalt and nickel, and pillars of oxide of a "B" metal selected from gallium, magnesium and zinc, or mixtures thereof.

DETAILED DESCRIPTIONS OF THE PREFERRED EMBODIMENTS

According to a preferred aspect of the present invention, the aluminum content in such catalytic materials is comprised within the range of from $1.10^{-4}$ to $1.10^{-1}$ mols per g of smectite, the molar ratio of "A" metal to aluminum is higher than 0 and smaller than, or equal to, 0.1, and the molar ratio of "B" metal to aluminum is larger than 0 and smaller than, or equal to 0.1.

Suitable smectites in the present invention preferably include bentonite, montmorillonite and beidellite.

The "B" metal is preferably selected from gallium, magnesium, or mixtures thereof. According to a preferred aspect, "B" metal is a mixture of gallium and magnesium.

The "A" metal preferably is cerium.

The catalysts according to the present invention are prepared by means of a process which comprises:

(a) preparing an aqueous solution containing aluminum ions, ions of an "A" metal selected from the group consisting of cerium, cobalt and nickel, and ions of a "B" metal selected from the group consisting of magnesium, zinc, gallium and mixtures thereof;

(b) adding an NaOH solution, in such a way that the molar ratio of Al:OH is comprised within the range of from 1.5 to 2.5, and, when also gallium ions are present, the molar ratio of Ga:OH is comprised within the range of from 1.5 to 2.5;

(c) keeping the reaction mixture at a temperature within the range of from 25° to 100° C., for 1–10 hours;

(d) bringing an aqueous suspension of a clay belonging to the family of smectites, into contact with the aqueous solution prepared in step (c) and keeping the resulting mixture at a temperature within the range of from 25° to 100° C. for 1–60 hours.

(e) separating the resulting solid material and calcining it at a temperature within the range of from 200° to 700° C.

In the (d) step, the aqueous suspension of smectite is preferably heated up to a temperature comprised within the range of from 25° to 50° C. before the aqueous solution prepared from the (c) step is added.

According to a preferred aspect, in the mixture prepared in the (d) step, the aluminum content is comprised within the range of from $1.10^{-4}$ to $1.10^{-1}$ mols per g of smectite, the molar ratio of "A" to aluminum is higher than 0 and lower than, or equal to, 0.1, and the molar ratio of "B" metal to aluminum is higher than 0 and lower than, or equal to, 0.1.

The catalysts of the present invention can be used in granular form, or, to facilitate their use in the stationary bed reactor, they can be advantageously used as cylindrical and spherical pellets obtained by means of traditional extrusion, agglomeration, pelletization techniques, or other well-known processes.

These catalysts make it possible to alkylate aromatic hydrocarbons with long chain olefins and achieve improved selectivity to linear alkylation products. The catalysts furthermore display high activity during long useful life times.

Therefore, a second object of the present invention is a process for the alkylation of aromatic hydrocarbons with linear olefins containing from 8 to 16 carbon atoms or mixtures thereof, which is carried out in the liquid phase, under anhydrous conditions and at a temperature comprised within the range of from 120° to 180° C., in the presence of a catalyst comprising a smectite which contains pillars of aluminum oxide, pillars of oxide of an "A" metal selected from cerium, cobalt and nickel, and pillars of oxide of a "B" metal selected from gallium, magnesium and zinc, or mixtures thereof.

According to a preferred aspect of the present invention, in such catalysts the aluminum content is comprised within the range of from $1.10^{-4}$ to $1.10^{-1}$ mols per g of smectite, the molar ratio of "A" metal to aluminum is higher than 0 and lower than, or equal to, 0.1, and the molar ratio of "B" metal to aluminum is higher than 0 and lower than, or equal to, 0.1.

The smectite is preferably selected from bentonite, montmorillonite and beidellite.

Preferably, a catalyst is used in which "B" is selected from gallium, magnesium, or a mixture thereof. According to a preferred aspect, "B" is a mixture of gallium and magnesium.

"A" preferably is cerium.

The aromatic hydrocarbons which can be alkylated are both monocyclic and polycyclic, and may also be alkyl-substituted. For example, benzene, toluene, xylenes, ethylbenzene, naphthalene, methyl-naphthalenes, ethyl-naphthalenes, anthracene, can be used. Benzene is the preferred substrate to alkylate. The alkylating agent is selected from olefins of from 8 to 16 carbon atoms, preferably of from 10 to 13 carbon atoms.

The process is preferably carried out under a pressure comprised within the range of from 10 to 50 bars, preferably of from 20 to 35 bars, at a WHSV (weight hourly space velocity) over the range of from 0.1 to 10 hours$^{-1}$, preferably of from 0.3 to 2 hours$^{-1}$.

Operating under anhydrous conditions is particularly important. The removal of water from the reactants can be carried out, e.g., by treatment with suitable molecular sieves. The catalyst is preferably pre-activated by treatment under a flowing nitrogen stream at a temperature comprised within the range of from 250° to 400° C., preferably of from 300° to 350° C., which removes any trace of water. The aromatic hydrocarbon and olefin are fed to the reaction vessel as a mixture, in a molar ratio of hydrocarbon:olefin comprised within the range of from 30:1 to 1:1, preferably of from 20:1 to 10:1.

The olefins can be diluted with n-paraffins containing from 8 to 16 carbon atoms, in a ratio comprised within the range of from 1:1 to 1:20.

The process according to the present invention can be carried out either batchwise, or continuously.

According to the first operating mode, the aromatic compound, the alkylating agent and the catalyst are charged to an autoclave. Pressure is supplied by means of the addition of an inert gas, e.g., nitrogen, helium or argon, while the alkylating agent is a liquid. If the alkylating agent is a gas, a portion of the operating pressure is supplied by the autogenous pressure of the gaseous alkylating agent, whilst the residual pressure portion is supplied by the presence of the inert gas. When the reaction has proceeded to completion, the autoclave is cooled down to room temperature, the system is vented, the autoclave is opened and the reaction mixture is recovered and the desired alkyl-aromatic species is isolated from it by means of traditional techniques, e.g., fractional distillation.

When the alkylation of the present invention is carried out in continuous mode, the catalyst is charged to a reactor, e.g., a tubular reactor, the pressure inside the reactor is adjusted at the desired operating pressure value and the catalyst is heated to the desired temperature. The reactants are then passed continuously through the catalyst bed at a selected space velocity value. The catalyst can be kept inside the reactor as a stationary bed, and the reactants are passed through it from the top downwards, or vice-versa, or as a mobile bed in which the catalyst and reactants flow through the reactor in the same direction, or counter-currently.

EXAMPLE 1

Preparation of Montmorillonite Containing Pillars of Alumina, Magnesium and Cerium Oxides (BTL-AlCeMg)

A volume of 250 ml of a 1M solution of NaOH is added dropwise, with stirring, to a solution prepared by mixing 500 ml of an 0.25M aqueous solution of $AlCl_3$, 2.7 g of $Ce(NO_3)_3.6H_2O$, 50 ml of $H_2O$ and 1.625 g of $Mg(NO_3)_2.6H_2O$. The resulting mixture is kept at 80° C. for 4 hours and is then added to a suspension of 20 g of natural montmorillonite, Bentolite$^{(R)}$ H (Laporte SCP) in 2.0 of water. The pH value is kept at 6. The suspension is kept stirred for 3 hours at 80° C. and then for 48 hours at room temperature. The solid material is recovered by centrifugation, is washed with deionized water to remove chloride ions, is dried in air at 100° C. and is calcined at 500° C.

EXAMPLE 2

Preparation of Montmorillonite Containing Pillars of Aluminum, Gallium and Cerium Oxides (BTL-AlGaCe)

A volume of 304.7 ml of a 1M solution of NaOH is added dropwise, with stirring, to a solution prepared by mixing 500 ml of an 0.25M aqueous solution of $AlCl_3$, 2.7 g of $Ce(NO_3)_3.6H_2O$ and 4.33 g of $Ga(NO_3)_3.9H_2O$. The resulting mixture is kept at 80° C. for 4 hours and is then added to a suspension of 20 g of natural montmorillonite, Bentolite$^{(R)}$ H (Laporte SCP) in 2.0 l of water. The suspension is stirred for 3 hours at 80° C., and then for 48 hours at room temperature. The solid material is recovered by centrifugation, is washed with deionized water to remove chloride ions, is dried in air at 100° C. and is calcined at 500° C.

EXAMPLE 3

Preparation of Montmorillonite Containing Pillars of Aluminum, Gallium, Cerium and Magnesium Oxides (BTL-AlGaCeMg)

A volume of 304.7 ml of a 1M solution of NaOH is added dropwise, with stirring, to a solution prepared by mixing 500 ml of an 0.25M aqueous solution of $AlCl_3$, 2.7 g of $Ce(NO_3)_3.6H_2O$, and 4.33 g of $Ga(NO_3)_3.9H_2O$, 1.625 g of $Mg(NO_3)_2.6H_2O$ and 50 ml of water. The resulting mixture is kept at 80° C. for 4 hours and is then added to a suspension of 20 g of natural montmorillonite, Bentolite$^{(R)}$ H (Laporte SCP) in 2.0 l of water. The suspension is stirred for 3 hours at 80° C. and for 48 hours at room temperature. The solid material is recovered by centrifugation, is washed with deionized water to remove chloride ions, is dried in air at 100° C. and is calcined at 500° C.

EXAMPLE 4

Comparison Example

Preparation of Montmorillonite Containing Alumina Pillars (BTL-Al)

A volume of 250 ml of a 1M solution of NaOH is added dropwise, with stirring, to 500 ml of an 0.25M aqueous solution of $AlCl_3$. The resulting mixture is kept with stirring at 80° C. for 4 hours and is then added to a suspension of 20 g of Bentolite$^{(R)}$ H in 2 l of water, kept at 80° C. After a 3-hour stirring, the solid material is recovered by centrifugation, is washed with deionized water to remove chloride ions, is dried in air at 100° C. and is calcined at 500° C.

EXAMPLE 5

Comparison Example

Preparation of Montmorillonite Containing Pillars of Aluminum and Cerium Oxides (BTL-AlCe)

A volume of 250 ml of a 1M solution of NaOH is added dropwise, with stirring, to a solution prepared by mixing 500 ml of an 0.25M aqueous solution of $AlCl_3$, 2.7 g of $Ce(NO_3)_3.6H_2O$ and 50 ml of $H_2O$. The resulting mixture is kept at 80° C. for 4 hours and is then added to a suspension of 20 g of Bentolite$^{(R)}$ H in 2 l of water. The pH value is kept at 6. The suspension is stirred for 3 hours at 80° C. and for 48 hours at room temperature. The solid material is recovered by centrifugation, is washed with deionized water to remove chloride ions, is dried in air at 100° C. and is calcined at 500° C.

EXAMPLE 6

Preparation of Montmorillonite Containing Pillars of Aluminum and Gallium Oxides (BTL-AlGa)

A volume of 304.7 ml of a 1M solution of NaOH is added dropwise, with stirring, to a solution prepared by mixing 500 ml of an 0.25M aqueous solution of $AlCl_3$, 2.7 g of $Ce(NO_3)_3.6H_2O$, 4.33 g di $Ga(NO_3)_3.9H_2O$, 1.625 g of $Mg(NO_3)_2.6H_2O$ and 50 ml of water. The resulting mixture is kept at 80° C. for 4 hours and is then added to a suspension of 20 g of Bentolite$^{(R)}$ H in 2.0 l of water. The suspension is stirred for 3 hours at 80° C. and then for 48 hours at room temperature. The solid material is recovered by centrifugation, is washed with deionized water to remove chloride ions, is dried in air at 100° C. and is calcined at 500° C.

EXAMPLE 7

Alkylation Test

For this test, a facility is used which is equipped with a tubular stainless steel reactor of 1 cm of inner diameter, equipped with temperature and pressure control means. In fact, inside the interior of the reactor a steel thermometer well of 0.3 cm of diameter was installed, inside which a thermocouple is inserted to read the temperature of the catalytic bed at various levels. Pressure control is carried out by means of an overflow valve installed at reactor outlet.

The process is carried out under a pressure of 30 bars and at a temperature of 155° C., and with a WHSV=0.65 h$^{-1}$.

The catalyst of Example 1, in form of pellets of 20–40 mesh of size is charged to the reactor in an amount of 3 g, so as to form an approximately 5 cm thick bed.

The alkylation reaction is carried out in liquid phase, by suitably controlling the process conditions.

The reactants are fed from the reactor top and the reactant feed consists of an olefin/paraffin blend added to benzene, in a molar ratio of benzene:olefins of 15:1. The feed is derived from a tank inside which it is kept under anhydrous conditions by using molecular sieves.

The composition of olefin/paraffin blend is reported in following table:

| Components | % by weight |
|---|---|
| n-$C_{10}$ paraffins | 8.49 |
| n-$C_{11}$ paraffins | 33.31 |
| n-$C_{12}$ paraffins | 24.34 |
| n-$C_{13}$ paraffins | 16.44 |
| total paraffins | 82.58 |
| n-$C_{10}$ olefins | 0.89 |
| n-$C_{11}$ olefins | 3.68 |
| n-$C_{12}$ olefins | 3.48 |

-continued

| Components | % by weight |
|---|---|
| n-$C_{13}$ olefins | 3.18 |
| total olefins | 11.23 |
| aromatics | 4.19 |
| diolefins | 0.10 |
| others | 1.90 |

The amount of olefins at reactor inlet is controlled by monitoring the bromine number of the feed; the conversion rate is determined by measuring the bromine number of effluent stream. The catalyst was pre-activated under a nitrogen stream at a temperature of 320°–330° C. in order to remove any residual trace of water.

The reactor is heated by means of an electrical tubular oven and the temperature control is carried out by means of a thermocouple installed inside the interior of the same oven.

The obtained results are summarized in the following table:

| Reaction time (hours) | Conversion rate (%) | LAB linearity (%) |
|---|---|---|
| 28.1 | 100 | 94.1 |
| 119 | 100 | 94.2 |
| 149.1 | 100 | 94.1 |
| 165.4 | 100 | 94.3 |
| 189.4 | 93.4 | 94.8 | wherein:
Conversion rate (% mol): (Consumed olefin mols/initial olefin mols).100
LAB linearity (% mol): (Mols of linear monoalkyl benzenes produced/mols of mono-alkyl benzenes produced).100

EXAMPLE 8

Alkylation Test

The process disclosed in above Example 6 is repeated using, as catalyst, the catalyst prepared in Example 2.

The obtained results are summarized in following table:

| Reaction time (hours) | Conversion rate (%) | LAB linearity (%) |
|---|---|---|
| 28.7 | 100 | 94.4 |
| 76 | 100 | 94.1 |
| 172 | 100 | 93.4 |
| 237.6 | 99.3 | 93.5 |

EXAMPLE 9

Alkylation Test

The process disclosed in above Example 6 is repeated using, as catalyst, the catalyst prepared in Example 3.

The obtained results are summarized in following table:

| Reaction time (hours) | Conversion rate (%) | LAB linearity (%) |
|---|---|---|
| 28.5 | 100 | 94.9 |
| 93.7 | 100 | 94.5 |
| 170.7 | 100 | 94.4 |
| 213.5 | 100 | 94.2 |
| 238.4 | 100 | 94.2 |

EXAMPLE 10

Comparison Alkylation Test

The process disclosed in above Example 6 is repeated using, as catalyst, the catalyst prepared in Example 4.

The obtained results are summarized in following table:

| Reaction time (hours) | Conversion rate (%) | LAB linearity (%) |
|---|---|---|
| 16.3 | 93.1 | 98.5 |
| 23.5 | 51.84 | 99.4 |
| 40.3 | 25.57 | 100 |

EXAMPLE 11

Comparison Alkylation Test

The process disclosed in above Example 4 is repeated using, as catalyst, the catalyst prepared in Example 5.

The obtained results are summarized in following table:

| Reaction time (hours) | Conversion rate (%) | LAB linearity (%) |
|---|---|---|
| 26.8 | 100 | 93.9 |
| 117.5 | 100 | 93.9 |
| 141.5 | 100 | 93.8 |
| 165.6 | 98.8 | 93.4 |

EXAMPLE 12

Comparison Alkylation Test

The process disclosed in above Example 4 is repeated using, as catalyst, the catalyst prepared in Example 6.

The obtained results are summarized in following table:

| Reaction time (hours) | Conversion rate (%) | LAB linearity (%) |
|---|---|---|
| 26.4 | 98.4 | 96.1 |
| 45 | 100 | 95.5 |
| 76 | 100 | 94.8 |
| 94 | 99.4 | 94.5 |

We claim:
1. A catalytic material, comprising:
a smectite containing pillars of aluminum oxide, pillars of an oxide of an "A" metal selected from the group consisting of cerium, cobalt and nickel, and pillars of an oxide of a "B" metal selected from the group consisting of gallium, magnesium, zinc, and mixtures thereof.

2. The catalytic material according to claim 1, in which the aluminum content is within the range of from $1\times10^{-4}$ to $1\times10^{-1}$ mols per gram of smectite, the molar ratio of "A" metal to aluminum is $>0$ and $\leq 0.1$, and the molar ratio of "B" metal to aluminum is $>0$ and $\leq 0.1$.

3. The catalytic material according to claim 1, in which smectite is selected from the group consisting of bentonite, montmorillonite and beidellite.

4. The catalytic material according to claim 1, in which the "B" metal is selected from gallium, magnesium, and mixtures thereof.

5. The catalytic material according to claim 1, in which the "B" metal is a mixture of gallium and magnesium.

6. The catalytic material according to claim 1, in which the "A" metal is cerium.

7. A process for preparing the catalytic material according to claim 1, which comprises:

(a) preparing an aqueous solution containing aluminum ions, ions of an "A" metal selected from the group consisting of cerium, cobalt and nickel, and ions of a "B" metal selected from the group consisting of magnesium, zinc, gallium and mixtures thereof;

(b) adding an NaOH solution, in such a way that the molar ratio of Al:OH is within the range of from 1.5 to 2.5, and, when also gallium ions are present, the molar ratio of Ga:OH is within the range of from 1.5 to 2.5;

(c) keeping the reaction mixture at a temperature within the range of from 25° to 100° C. for 1–10 hours;

(d) bringing an aqueous suspension of a clay belonging to the family of smectites, into contact with the aqueous solution prepared in step (c) and keeping the resulting mixture at a temperature within the range of from 25° to 100° C. for 1–60 hours; and (e) separating the resulting solid material and calcining it at a temperature within the range of from 200° to 700° C.

8. The process according to claim 7, in which in the mixture prepared in step (d), the aluminum content is comprised within the range of from $1\times10^{-4}$ to $1\times10^{-1}$ mols per gram of smectite, the molar ratio of the "A" metal to aluminum is $>0$ and $\leq 0.1$, and the molar ratio of the "B" metal to aluminum is $>0$ and $\leq 0.1$.

* * * * *